（12) United States Patent
Pelletier et al.

(10) Patent No.: US 12,006,821 B2
(45) Date of Patent: *Jun. 11, 2024

(54) BANDGAP DETECTION OF REACTIVE COMPONENTS IN FLUIDS

(71) Applicant: Halliburton Energy Services, Inc., Houston, TX (US)

(72) Inventors: Michael T. Pelletier, Houston, TX (US); David L. Perkins, Forks Township, PA (US); Christopher Michael Jones, Katy, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 352 days.

This patent is subject to a terminal disclaimer.

(21) Appl. No.: 17/175,180

(22) Filed: Feb. 12, 2021

(65) Prior Publication Data

US 2021/0164908 A1 Jun. 3, 2021

Related U.S. Application Data

(63) Continuation of application No. 15/533,370, filed as application No. PCT/US2016/052472 on Sep. 19, 2016, now Pat. No. 10,962,484.

(51) Int. Cl.
*E21B 49/08* (2006.01)
*G01N 21/77* (2006.01)
(Continued)

(52) U.S. Cl.
CPC ............ *E21B 49/087* (2013.01); *E21B 49/08* (2013.01); *G01N 21/77* (2013.01); *G01N 27/12* (2013.01);
(Continued)

(58) Field of Classification Search
None
See application file for complete search history.

(56) References Cited

U.S. PATENT DOCUMENTS

| 4,495,793 A | 1/1985 | Hager |
| 7,362,422 B2 | 4/2008 | DiFoggio et al. |

(Continued)

FOREIGN PATENT DOCUMENTS

| WO | 1999000575 A2 | 1/1999 |
| WO | 200163094 A1 | 8/2001 |

(Continued)

OTHER PUBLICATIONS

PCT Application Serial No. PCT/US2016/052472, International Search Report, mailed May 10, 2017, 3 pages.

(Continued)

*Primary Examiner* — Lore R Jarrett
(74) *Attorney, Agent, or Firm* — DeLizio, Peacock, Lewin & Guerra, LLP

(57) ABSTRACT

The present application relates sensing reactive components in fluids by monitoring band gap changes to a material having interacted with the reactive components via physisorption and/or chemisorption. In some embodiments, the sensors of the present disclosure include the material as a reactive surface on a substrate. The band gap changes may be detected by measuring conductance changes and/or spectroscopic changes. In some instances, the sensing may occur downhole during one or more wellbore operations like drilling, hydraulic fracturing, and producing hydrocarbons.

20 Claims, 7 Drawing Sheets

(51) Int. Cl.
*G01N 27/12* (2006.01)
*G01N 33/28* (2006.01)

(52) U.S. Cl.
CPC ...... *G01N 33/2823* (2013.01); *E21B 49/0875* (2020.05); *G01N 2021/7773* (2013.01); *G01N 2021/7783* (2013.01)

(56) References Cited

U.S. PATENT DOCUMENTS

| | | | |
|---|---|---|---|
| 10,962,484 | B2* | 3/2021 | Pelletier .................. G01V 7/00 |
| 2003/0030786 | A1* | 2/2003 | Shurgalin ............... G01M 11/31 356/73.1 |
| 2007/0034793 | A1 | 2/2007 | Estes et al. |
| 2007/0143023 | A1 | 6/2007 | Betancourt et al. |
| 2009/0009768 | A1 | 1/2009 | Jiang et al. |
| 2009/0114013 | A1 | 5/2009 | DiFoggio |
| 2009/0153845 | A1 | 6/2009 | DiFoggio |
| 2010/0177310 | A1 | 7/2010 | DiFoggio |
| 2010/0269579 | A1 | 10/2010 | Lawrence et al. |
| 2012/0021524 | A1 | 1/2012 | van Hal et al. |
| 2013/0068940 | A1* | 3/2013 | Jones ..................... E21B 49/00 252/408.1 |
| 2014/0166871 | A1 | 6/2014 | Jamison et al. |
| 2014/0338900 | A1 | 11/2014 | Jones et al. |
| 2015/0330215 | A1 | 11/2015 | Jamison et al. |
| 2016/0299084 | A1* | 10/2016 | Price .................. G01N 21/8422 |
| 2020/0141874 | A1 | 5/2020 | Pelletier et al. |

FOREIGN PATENT DOCUMENTS

| | | |
|---|---|---|
| WO | 2008042866 A2 | 4/2008 |
| WO | 2010083386 A2 | 7/2010 |
| WO | 2011146068 A1 | 11/2011 |
| WO | 2014018002 A1 | 1/2014 |
| WO | 2014042642 A1 | 3/2014 |
| WO | 2016032435 A1 | 3/2016 |
| WO | 2017127411 A1 | 7/2017 |

OTHER PUBLICATIONS

PCT Application Serial No. PCT/US2016/052472, International Written Opinion, mailed May 10, 2017, 6 pages.
European Application Serial No. EP 16 916 379.7; Communication Pursuant To Article 94(3); Apr. 7, 2020, 6 pages.
European Application Serial No. EP 16 916 379.7; European Search Report; May 22, 2019, 9 pages.
U.S. Appl. No. 15/533,370, Final Office Action, mailed Dec. 16, 2020, 11 pages.
U.S. Appl. No. 15/533,370, Non-Final Office Action, mailed Sep. 18, 2020, 11 pages.

* cited by examiner

BANDGAP DETECTION OF REACTIVE COMPONENTS IN FLUIDS

BACKGROUND

The present application relates sensing reactive components in fluids.

Hydrocarbon producing wells may contain many different formation liquids and gases such as methane, ethane, and other higher hydrocarbons, as well as carbon dioxide, hydrogen sulfide, water, and other compounds. In order to evaluate the commercial value of a hydrocarbon producing well, or as an aid in operations and well planning, it is often useful to obtain information by analyzing the component concentrations of the produced fluid from a formation or an individual well.

For example, certain components in downhole fluids are corrosive. In general, there are four types of corrosion: sweet, sour, oxygen, and electrochemical. Sour corrosion is found in oil and gas wells that contain hydrogen sulfide gas. Hydrogen sulfide also presents health risks that need to be addressed and planned for. Wells may also produce other undesirable corrosive components such as carbon dioxide. A good understanding of the downhole fluid and gas concentrations is desirable in an attempt to control corrosion rates and to plan for safe development and production of the hydrocarbons.

Spectroscopy is a known technique for analyzing downhole fluids, including drilling fluids and crude oil. For example, methods are known for analyzing drilling muds that involve reflectance or transmittance infrared (IR) spectroscopy that assays the components of the fluid directly. Spectroscopy is typically employed in wellbore environments in the near infrared-range of from 1000 to 2500 nm. Spectroscopy is typically emitted in this range because near IR emitters and sensors are known to be easier to operate at well temperatures while longer wavelength emitters have shown limited output optical power under similar well conditions.

Typically, spectroscopy monitoring involves obtaining a formation fluid sample downhole and bringing the sample to the surface where measurements and processing of the resultant data takes place. These measurement methods are typically utilized at relatively large time intervals and thus do not provide continuous information about wellbore condition or that of the surrounding formations.

BRIEF DESCRIPTION OF THE DRAWINGS

The following figures are included to illustrate certain aspects of the embodiments, and should not be viewed as exclusive embodiments. The subject matter disclosed is capable of considerable modifications, alterations, combinations, and equivalents in form and function, as will occur to those skilled in the art and having the benefit of this disclosure.

DESCRIPTION

Figure 1:
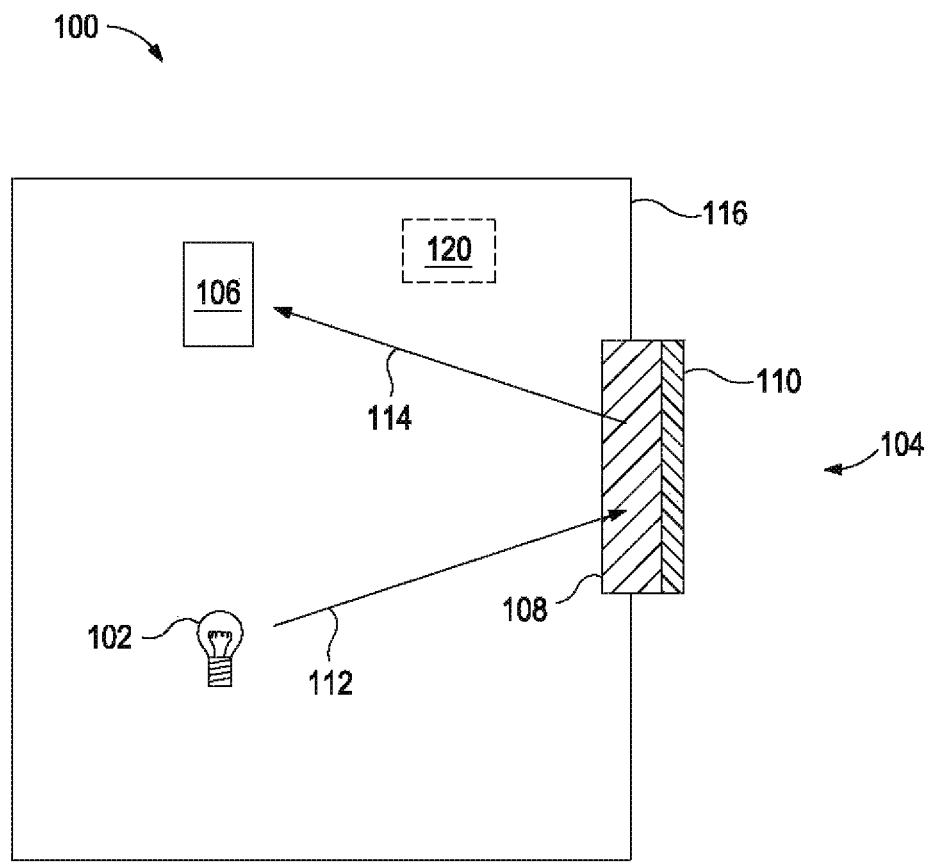
FIG. 1 illustrates a configuration for a backside reflectance sensor of the present disclosure.

The present application relates sensing reactive components in fluids by monitoring band gap changes to a material having interacted with the reactive components via physisorption and/or chemisorption. In some embodiments, the sensors of the present disclosure include the material as a reactive surface on a substrate. The band gap changes to the material may be detected by measuring conductance changes and/or spectroscopic changes. In some instances, the sensing may occur downhole during one or more wellbore operations like drilling, hydraulic fracturing, and producing hydrocarbons.

As used herein, the term "physisorption" and grammatical derivations thereof refer to physical adsorption of a compound to a material without the compound chemically reacting with the material. As used herein, the term "chemisorption" and grammatical derivations thereof refer to adsorption of a compound to a material where the compound and the material chemically react. As used herein, the term "reactive component" refers to the components of a fluid that when physisorbed or chemisorbed to a material cause the band structure of the material to change. As used herein, the term "reactive surface" refers to portion of the material that is monitored for band gap changes when contacted with the reactive component. The portion of the material that is the reactive surface is the distance extending across the material over an optical interaction depth for that material. For most opaque materials, this optical interaction depth would be limited to generally more than a quarter wavelength of light to a few wavelengths of light (small distances). However, for some opaque materials, the optical interaction depth can be enhanced by various evanescent enhancement techniques. For transparent materials, the optical interaction depth extends to the entire limit of diffusion distance through the material. Although this may enhance the optical activity of the material, it will generally slow the response time of the measurement. The optimal response time and diffusion characteristics of the surface material will allow a sufficient distance through the surface to be identified. Practically, optical interaction depth may be less than a few nanometers to a few microns for opaque systems, and possibly up to a few millimeters (maybe a centimeter for large systems) that are transparent.

The sensors described herein utilize reactive surfaces formed of materials whose electronic band structure changes when reactive components in fluids are physisorbed and/or chemisorbed thereto. The change to the reactive surfaces' band structure can then be detected via reflectance spectroscopy, transmission spectroscopy, electrical measurements, or a combination thereof and used to determine the concentration of the reactive components in fluids including downhole fluids like drilling fluids, formation fluids (i.e., fluids native to the formation), acidizing fluids, hydrocarbon fluids, and the like.

It should be noted that the methods and systems of the present discourse are different than surface enhanced spectroscopy methods like surface enhanced Raman where the band structure of the reactive component is measured. Rather, the present methods and systems measure changes to the bands structure of reactive surfaces. Because the reactive surface is being analyzed in the methods and systems described herein, the sensor of the present disclosure may be sensitive to lower concentrations of the reactive components.

Additionally, the methods and systems of the present discourse are more robust than surface enhanced spectroscopy methods because the environment downhole may be hostile (e.g., high temperature, high pressure, corrosive, and the like). The hostile downhole environment would likely introduce significant error to Raman spectroscopic methods because the high temperature may shift the laser light frequency and vibrations may disturb the optics, which would increase the noise and make signal detection more difficult.

The reactive components in the fluid that may be analyzed with the sensors described herein may include, but are not limited to, hydrogen sulfide, mercury, carbon dioxide, acidic chemicals (e.g., hydrochloric acid, sulfuric acid, and hydrofluoric acid), caustic chemicals (e.g., sodium hydroxide and calcium hydroxide), and the like, and combinations thereof. In some instances, reactive components like mercury may be of interest because of environmental concerns. In some instances, reactive components like hydrogen sulfide and carbon dioxide may be of interest because of corrosion concerns. The sensors described herein may be useful in estimating or otherwise determining the concentration of one or more reactive components in fluids.

In some instances, the sensors described herein may be sensitive to a class of chemicals like acidic chemicals or caustic chemicals rather than a specific chemical. Accordingly, the sensors may be useful in estimating or otherwise determining the concentration or strength of the class of chemicals. For example, the substrate may react with acidic chemicals and be useful in determining a pH, acidic strength, or corrosive potential of the fluid.

Backside Reflectance Sensors

In some instances, the sensors may utilize a backside reflectance technique where the light used in the spectroscopy does not travel through the fluid. This eliminates the contents of the fluid from providing interference to the measurement due to unintended alteration of the light. For sufficiently transparent fluids (in the optical region of interest) a reflectance through the fluid may be advantageous. For example, the opacity of the oil-based fluid or the light scattering effect of emulsion particles in emulsified fluids may alter the light and interfere with measurements and analyses described herein. However, the backside reflectance sensors described herein may also be used in conjunction with water-based fluids and gases.

FIG. 1 illustrates a configuration for a backside reflectance sensor 100 of the present disclosure. The backside reflectance sensor 100 comprises a light source 102, a sensing component 104, and a detector 106. The sensing component 104 includes a substrate 108 and a reactive surface 110. Light 112 from the light source 102 passes through the substrate 108, impinges the reactive surface 110, and is reflected as interacted light 114, which is detected by the detector 106. As illustrated, the light source 102, the sensing component 104, and the detector 106 are contained in a housing 116. However, in some instances, the light source 102 and the detector 106 may be outside the housing 116 where fiber optics are used to convey the light 112 and the interacted light 114 in and out of the housing 116 and to and from the sensing component 104.

In use, a fluid comprising one or more reactive components contacts the sensing component 104 where the relative components physisorb or chemisorb to the reactive surface 110, which changes the band structure of the reactive surface 110 (i.e., the material that the reactive surface 110 is composed of). The band structure changes are then measured using the detector 106 and a concentration of the reactive components may be determined, as described further below.

The reactive surface 110 should have a thickness sufficiently thin to observe the change to the reactive surface 110 at the substrate 108 and sufficiently thick to be robust for the measurement location (e.g., downhole). The thickness of the reactive surface 110 may depend on the composition of the reactive surface 110, the size or diffusion rate of the reactive component relative to the porosity of the reactive surface 110, and the like. The reactive surface 110 may have a thickness ranging from about 10 nm to about 3 mm including subsets therebetween. For example, an opaque reactive surface 110 may have a thickness ranging from about 10 nm to about 3 microns including subsets therebetween like about 10 nm to about 50 nm, about 10 nm to about 100 nm, about 50 nm to about 500 nm, about 100 nm to about 3 microns, about 500 nm to about 3 microns, or about 1 micron to about 3 microns. For a transparent reactive surface 110 where backscattered interacted light 114 is measured, the thickness of the reactive surface 110 may range from about 10 nm to about 3 mm, including subsets therebetween. In some instances, the thickness of the reactive surface 110 may vary (tapered or stepped) across the substrate 108, which allows for an added dynamic range of the sensor. By way of nonlimiting example, a reactive surface 110 of silver may taper across the substrate 108 from 100 nm thickness to 100 micron thickness. Then, over time when interacted with hydrogen sulfide, the hydrogen sulfide diffuses deeper into the reactive surface 110 and change the gradient of total reflectivity of the silver. Driven by the total amount of hydrogen sulfide encountered, the concentration of hydrogen sulfide may be calculated based on the fluid flow rate and signal output where a large change in signal output and low flow rate, for example, would indicate a high concentration of hydrogen sulfide.

The reactive surface 110 may be formed on the substrate 108 by a plurality of methods. In some instances, the reactive surface 110 may be a foil or thin film that is attached (e.g., via sintering) to the substrate 108. In some instances, the reactive surface 110 may be sputter coated, deposited via chemical vapor deposition, deposited via ion vapor deposition, or the like onto the substrate 108. In some embodiments, the coating may be further annealed to the substrate.

In some embodiments, the reactive surface 110 may be formed of particles that are deposited on the substrate 108 via liquid phase deposition. Such particles may have an average diameter of about 1 nm to about 3 microns, including subsets therebetween like about 1 nm to about 100 nm, about 1 nm to about 500 nm, about 100 nm to about 1 micron, about 500 nm to about 3 microns, about 1 micron to about 3 microns, or about 500 nm to about 1 micron. In some instances, the particles may be deposited as a monolayer or substantially a monolayer (i.e., at least 90% by area being a monolayer) on the substrate 108. Additionally, in some instances, more than one type of particle (e.g., copper particles and molybdenum particles) may be used where each react with different reactive components or with the same reactive component at different rates.

Exemplary materials that the reactive surface 110 may be composed of may include, but are not limited to, gold, nickel, copper, molybdenum, aluminum, tungsten, titanium, and the like, and any combination thereof. For example, copper and molybdenum turn black when exposed to hydrogen sulfide. In another example, aluminum reacts with mercury and not hydrogen sulfide.

The substrate 108 may be composed of materials that include, but are not limited to, sapphire ($Al_2O_3$), germanium, zinc selenide, calcium fluoride, manganese fluoride, fused silica, quartz, and the like. The composition of the substrate 108 should be chosen to be transparent to the wavelengths of the light 112 and interacted light 114 necessary for detecting the physisorption or chemisorption of the reactive component of interest while also being inert to the reactive component of interest.

The light 112 may be any suitable wavelength of electromagnetic radiation for detecting changes to the band structure of the reactive surface 110. Exemplary lights 112 may include, but are not limited to, visible light, ultraviolet light, infrared light, and the like, and any combination thereof. Exemplary light sources 102 may include, but are not limited to, a light bulb, a light emitting diode (LED), a laser, a blackbody, a photonic crystal, an X-Ray source, and the like, and any combination thereof.

Exemplary detectors 106 may include, but are not limited to, a thermal detector such as a thermopile or photoacoustic detector, a semiconductor detector, a piezo-electric detector, a charge coupled device (CCD) detector, a video or array detector, a split detector, a photon detector (such as a photomultiplier tube), photodiodes, and the like, and any combination thereof.

In some instances, the backside reflectance sensor 100 may include more than one sensing component 104 for detecting the concentration of different reactive components. For example, a single light source 102 may be used and multiple detectors for measuring the interacted light 114 corresponding to each of the sensing components 104. In another example, each of the more than one sensing component 104 may have a corresponding light source 102 and detector 106. In yet another example, when the interacted light 114 for two or more sensing components 104 do not interfere, a single light source 102 and detector 106 may be used with two or more sensing components 104.

In some instances, the backside reflectance sensor 100 may further comprise light filters and optical computing devices (e.g., commonly owned U.S. Pat. Nos. 6,198,531, 6,529,276, 7,123,844, 7,834,999, 7,911,605, 7,920,258, and 8,049,881) anywhere along the optical path from the light source 102 to the detector 106.

In some instances, backside reflectance sensor 100 may be configured for regenerating the reactive surface 110. For example, in some instances, increasing the temperature and decreasing the concentration of the reactive components in contact with the reactive surface 110 may desorb the reactive components physisorbed or chemisorbed to the reactive surface 110, which would return the band structure of the reactive surface 110 closer to the original band structure. Then, the reactive surface 110 after regeneration may be exposed to the fluid with reactive components therein for additional measurements.

Therefore, in some instances, the backside reflectance sensor 100 may optionally further include a heating element 120 for regenerating the reactive surface 110. In some instances, the backside reflectance sensor 100 may optionally include flow paths and valves (not illustrated) that allow for stopping flow of the fluid and starting flow of a purge fluid (e.g., water, cleaning fluids, inert gases, air, and the like) for regenerating the reactive surface 110. In some instances, the purge fluid may include scavengers that preferentially bind to or react with the reactive components to further drive desorption from the reactive surface 110.

Transmission Sensors

In some instances, the sensors may utilize a transmission technique where the light used in the spectroscopy travels through the fluid. This sensor may be useful in analyzing reactive components in water-based fluids or gases that are sufficiently transparent and non-scattering to interfere with the spectroscopy.

Figure 2:
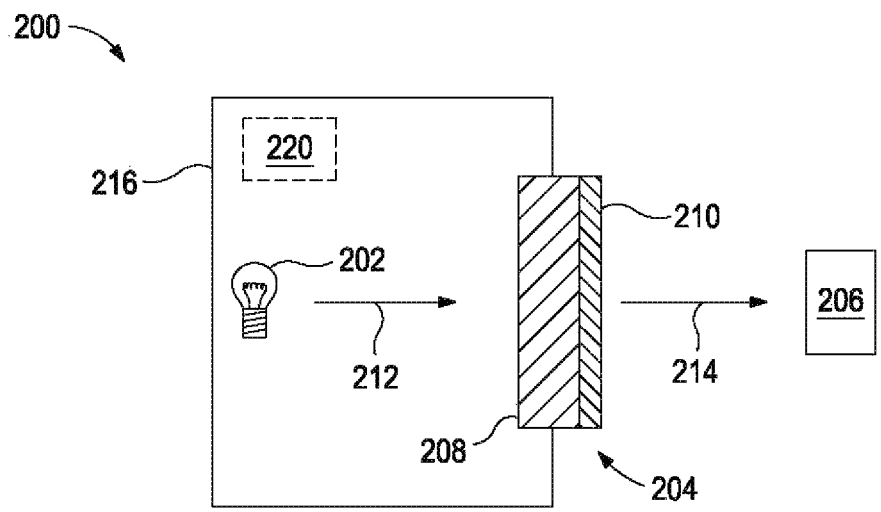
FIG. 2 illustrates a configuration for a transmission sensor of the present disclosure.

FIG. 2 illustrates a configuration for a transmission sensor 200 of the present disclosure. The transmission sensor 200 comprises a light source 202, a sensing component 204, and a detector 206. The sensing component 204 includes a substrate 208 and a reactive surface 210. Light 212 from the light source 202 passes through the substrate 208 and reactive surface 210 to produce interacted light 214, which is detected by the detector 206. As illustrated, the light source 202 and the sensing component 204 are contained in a housing 216. However, in some instances, the light source 202 may be outside the housing 216 where fiber optics are used to convey the light 212 into the housing 216 and to the sensing component 204.

Figure 3:
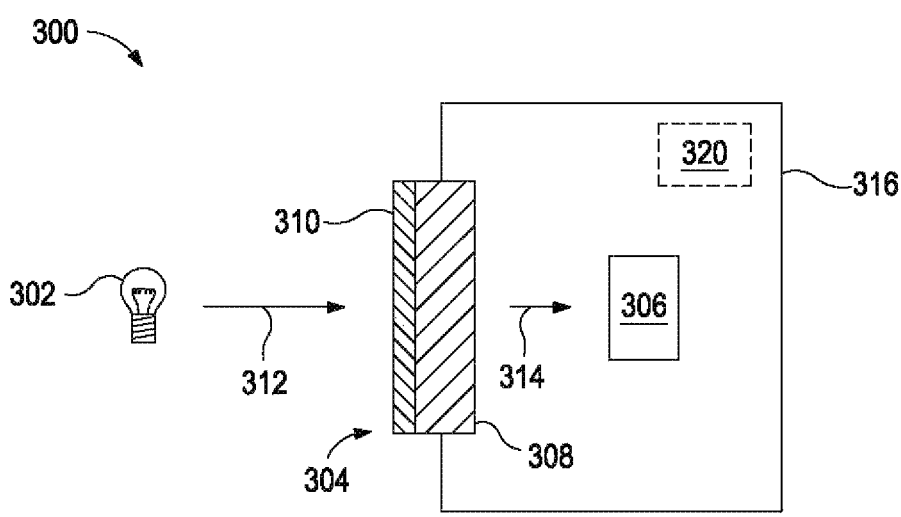
FIG. 3 illustrates an alternative configuration for a transmission sensor of the present disclosure.

FIG. 3 illustrates an alternative configuration for a transmission sensor 300 of the present disclosure. The transmission sensor 300 comprises a light source 302, a sensing component 304, and a detector 306. The sensing component 304 includes a substrate 308 and a reactive surface 310. Light 312 from the light source 302 passes through the substrate 308 and reactive surface 310 to produce interacted light 314, which is detected by the detector 306. As illustrated, the detector 306 and the sensing component 304 are contained in a housing 316. However, in some instances, the detector 306 may be outside the housing 316 where fiber optics are used to convey the interacted light 314 out of the housing 316 and to the detector 306.

In use, a fluid comprising one or more reactive components contacts the sensing component 204,304 where the relative components physisorb or chemisorb to the reactive surface 210,310, which changes the band structure of the material that the reactive surface 210,310 is composed of. The band structure changes are then measured using the detector 206,306 and a concentration of the reactive components may be determined, as described further below.

Generally, the substrate 208,308, light source 202,302, and detector 206,306 may be the same as the substrate 108, light source 102, and detector 106 described relative to FIG. 1. The reactive surface 210,310, however, should be configured for transmission spectroscopy. For example, a monolayer or less of particles may be deposited on the substrate 208,308 in a density that allows for the light 212,312 to interact with the particles to form interacted light 214,314 that is measured by the detector 206,306. In some instances, the reactive surface 210,310 may comprise a matrix that is nonreactive to the reactive component and is doped with a material that changes band gap when contacted/reacted with the reactive component. For example, a permeable matrix like an open cell foam polymer may be doped with copper and/or molybdenum particles that react with hydrogen sulfide.

The reactive surface 210,310 may have a thickness ranging from about 10 nm to about 3 mm, including subsets therebetween like about 10 nm to about 100 nm, about 10 nm to about 500 nm, about 100 nm to about 1 micron, about 500 nm to about 3 microns, about 1 micron to about 3 microns, or about 500 nm to about 1 micron.

In some instances, the transmission sensor 200,300 may include more than one sensing component 204,304 for detecting the concentration of different reactive components. Suitable configurations may include those described relative to the backside reflectance sensor 100 with more than one sensing component 104.

In some instances, transmission sensor 200,300 may be configured for regenerating the reactive surface 210 and optionally include a heating element 220,320 and flow paths and valves (not illustrated) as described relative to regenerating the reactive surface 110 in FIG. 1.

Electronic Sensors

In some instances, the sensors may utilize an electrical technique where the conduction or resistance of the reactive surface is used to analyze the concentration of the reactive components in the fluid.

Figure 4:
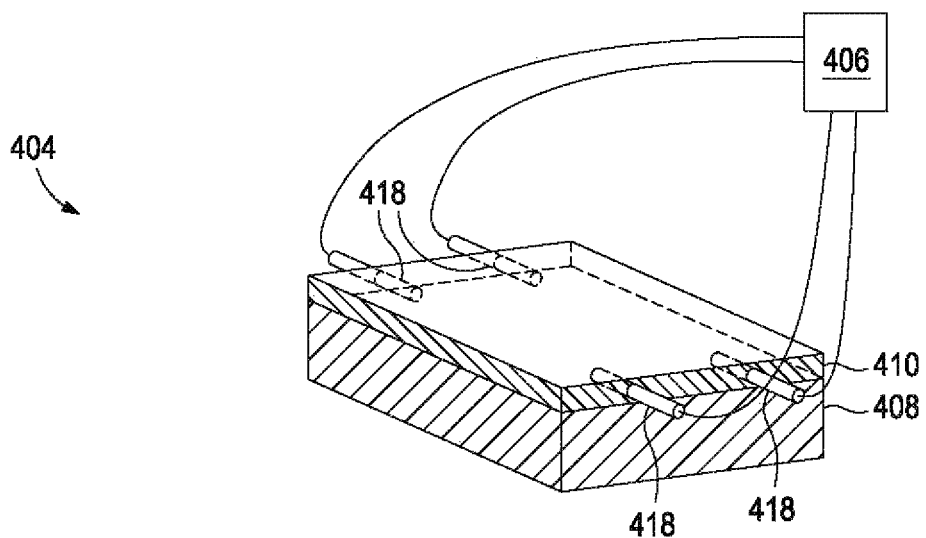
FIG. 4 illustrates a configuration for an electrical sensing component of the present disclosure.

FIG. 4 illustrates a configuration for an electrical sensing component 404 of the present disclosure. The sensing component 404 includes a substrate 408, a reactive surface 410, and electrical leads 418 contacting (e.g., illustrated as embedded in) the reactive surface 410. In use, a fluid comprising one or more reactive components contacts the sensing component 404 where the relative components physisorb or chemisorb to the reactive surface 410, which changes the band structure of the material that the reactive surface 410 is composed of. The band structure changes are then measured using the detector 406 connected to the electrical leads 418 and a concentration of the reactive components may be determined, as described further below.

Generally, the substrate 408 is an insulator that does not interfere with the electrical measurements of the reactive surface 410, which may be the same as the substrate 108 described relative to FIG. 1. Further, such substrate materials may further allow for simultaneously performing spectroscopic detection methods described herein. When spectroscopic methods are not employed, the substrate 408 may be an opaque, non-conductive material like polytetrafluoroethylene.

The reactive surface 410 may be any conductive material that changes band structures when contacted by a reactive components of interest. Exemplary materials may include, but are not limited to, copper, polyethyleneimine, and the like, and any combination thereof. For example, the reactive surface 410 may comprise polyethyleneimine that selectively absorbs carbon dioxide, which cause the band structure of polyethyleneimine and, consequently, the conductance of polyethyleneimine to change.

The reactive surface 410 may have a thickness ranging from about 10 nm to about 3 mm, including subsets therebetween like about 10 nm to about 100 nm, about 10 nm to about 500 nm, about 100 nm to about 1 micron, about 500 nm to about 3 microns, about 1 micron to about 3 microns, or about 500 nm to about 1 micron.

Exemplary detectors 406 for measuring the electrical properties of the reactive surface 410 may include, but are not limited to, a voltmeter.

In some instances, the sensor may include more than one sensing component 404 for detecting the concentration of different reactive components.

In some instances, an electrical sensor may be configured for regenerating the reactive surface 410 and optionally include a heating element, flow paths, and valves (not illustrated) as described relative to regenerating the reactive surface 110 in FIG. 1.

Combination Sensors

In some instances, the sensors may utilize both spectroscopic and electrical techniques to analyze the concentration of the reactive components in the fluid.

Figure 5:
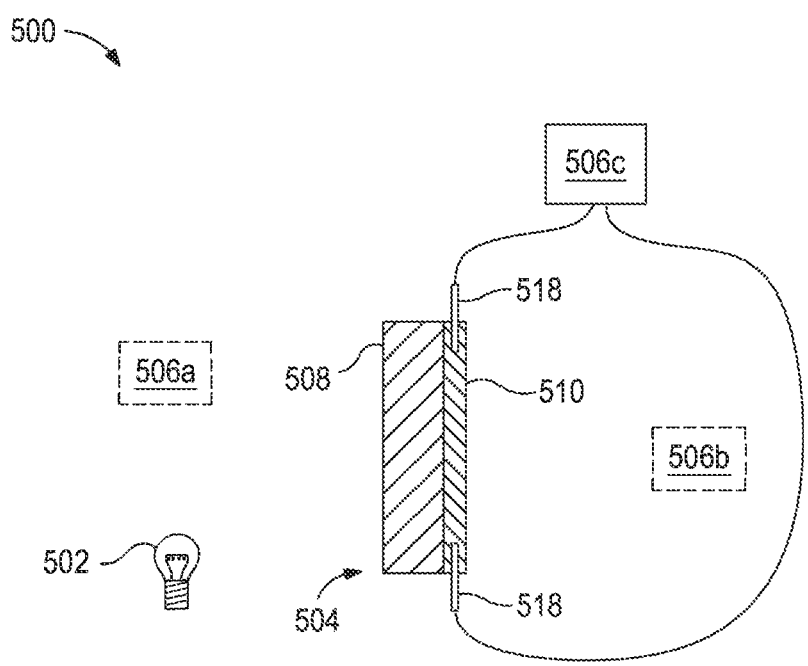
FIG. 5 illustrates a configuration for a combination sensor of the present disclosure.

FIG. 5 illustrates a configuration for a combination sensor 500 of the present disclosure. The combination sensor 500 comprises a light source 502, a sensing component 504, a conductance detector 506c, and either spectroscopic detector 506a or 506b based on the combination sensor using backside reflectance or transmission spectroscopic techniques, respectively. The sensing component 504 includes a substrate 508, a reactive surface 510, and electrical leads 518 contacting the reactive surface 510 and connected to the conductance detector 506c. The combination sensor 500 may further including a housing (not shown) similar to one of housings 116,216,316 of FIGS. 1-3 based on the desired spectroscopic detection mode.

The substrate 508 may be composed of a material as described relative to the substrate 108 of FIG. 1, the substrate 208 of FIG. 2, or the substrate 308 of FIG. 3 to allow for the spectroscopic analysis techniques or the substrate 408 of FIG. 4 to allow for the electrical analysis techniques.

The reactive surface 510 should be chosen to allow for both the spectroscopic and electrical techniques. For example, copper substrates may be useful when employing backside reflection and electrical techniques. In another example, a polyethyleneimine matrix with particles of aluminum may be useful for transmission and electrical techniques in detecting and/or monitoring carbon dioxide and mercury concentrations.

By way of nonlimiting example, a conductance detector 506c may be combined with either spectroscopic detector 506a or 506b where the conductance detector 506c is used as an electrochemical cell to generate reagents in situ. For example, in a brine, the electrochemical cell could generate a diffusion limited volume close to the reactive surface 510. With a sodium chloride brine, for example, a drive voltage of 1.5 V would generate sodium hydroxide at the cathode and chlorine gas at the anode. The chloride is a strong oxidizing agent that may react with a reactive component in the fluid via halogen substitution. The resultant molecule may then react with the reactive surface 510 and be measured. Additionally, the sodium hydroxide will neutralize any residual acid causing the local environment at the cathode to be caustic, which stabilized sulfide ions and allows for reaction with the reactive surface 510 and measurement of the sulfide ion concentration.

By way of another nonlimiting example, some oils (used as the carrier fluid) have a fair amount of residual organic acids therein that may be quantitatively neutralized with the electrochemical cell described above.

Systems and Methods for Analyzing the Concentration of Reactive Components

The sensors described herein (e.g., those described relative to FIGS. 1-5 and variations thereof) rely on equilibrium laws to calculate a concentration of reactive components in the fluid. The sensors described herein may measure an absolute value and/or a rate of change for the spectroscopic and/or electrical measurements of the reactive surface.

When using the absolute value, the reactive components and reactive surface may be allowed to come to a chemical equilibrium where there is substantially no net change (less than 5% net change per minute) in the concentration of species involved in the chemical reaction. The chemical equilibrium will be reflected in a stabilization of the sensor response. As used herein, "stabilization" does not necessarily mean that no spectroscopic or electrical change is occurring but is inclusive of small changes that indicate chemical equilibrium is being approached. In some instances, a spectroscopic or electrical change of less than 20% (preferably less than 5%) per measurement cycle (e.g., a 1 millisecond measurement cycle to a 10 minute measurement cycle) may indicate stabilization of the sensor response and, consequently, an approach to chemical equilibrium. Specific sensor configurations, reactive surfaces, and reactive components may have higher or lower tolerances for sufficient equilibrium. This tolerance for stabilization of the sensor may be guided by the accuracy of the desired measurement. Measurement cycles are typically from milliseconds (for example for pressure sensing) to tens of minutes (for example for mobility measurements) for wireline testers, but may be on the order of days to weeks for pipeline monitoring. Each application will have its own defined useful measurement cycle. The absolute value at equilibrium may be compared to a known correlation between concentration of the reactive components and the spectroscopic and/or electrical measurements, which may be in the form of a table, graph, equation, or the like. The known correlation between concentration of the reactive components and the spectroscopic and/or electrical measurements may be determined experimentally or modeled mathematically.

The correlation between concentration of the reactive components and the spectroscopic and/or electrical measurement may be temperature dependent. Accordingly, the temperature at or near the sensor may be measured or estimated. In some instances, the sensor (e.g., those described relative to FIGS. 1-5) may optionally further include a temperature sensor and or pressure sensor.

Further, the correlation between concentration of the reactive components and the spectroscopic and/or electrical measurement may be dependent on flow rate of the fluid across the reactive surface. For example, at higher flow rates, the reactive components have less time to interact with the reactive surface. Therefore, the absolute change of the spectroscopic and/or electrical measurements at equilibrium may be lower than for a slower flow rate. Therefore, the correlation between concentration of the reactive components and the spectroscopic and/or electrical change may account for flow rate (e.g., by including a flow rate proportionality factor).

Performing the analysis using the absolute value of the spectroscopic and/or electrical measurement at equilibrium may require a significant wait time (e.g., several hours) to allow the reactive components and reactive surfaces to come to equilibrium. Accordingly, the rate of change of the spectroscopic and/or electrical measurements as the reactive components and reactive surfaces to come to equilibrium may be used to determine or estimate the concentration of the reactive components in the fluid.

When using a rate of change of the spectroscopic and/or electrical measurements, the rate of change may be compared to an equilibrium constant of the reaction between the reactive components and the reactive surfaces, which again may be temperature and/or flow rate dependent. Similar to the absolute measurements, a correlation between concentration of the reactive components and the rate of change of the spectroscopic and/or electrical measurements may be determined experimentally or modelled mathematically and used to determine the concentration of the reactive components in the fluid.

In some embodiments, the sensors described herein (e.g., those described relative to FIGS. 1-5 and variations thereof) may be coupled to control system (e.g., a processor), which may optionally be part of the sensor itself. The control system, described further below, may include the absolute and/or rate of change correlations described herein between the concentration of the reactive components and the spectroscopic and/or electrical measurements and provide an estimated concentration of the reactive components in the fluid.

In some instances, based on the concentration of the reactive components, an action in the present wellbore operation or a subsequent operation may be taken. For example, if a zone within a formation is determined to have a high concentration of a reactive component like hydrogen sulfide, mercury, or carbon dioxide, that zone may be isolated to mitigate production of hydrocarbon fluids with such reactive components. In another example, during drilling or stimulation, it may be determined that the fluids in the formation have a high concentration of a corrosive reactive component like hydrogen sulfide or carbon dioxide. Then, the tools used in the production operation may be composed of materials that are less susceptible to corrosion. In yet another example, sensors may be included on tools in use to monitor a cumulative amount of reactive components encountered. Then, when a threshold amount of the reactive component exposure is reached for the tool or a component thereof is reached, the tool or component thereof may be replaced, which may mitigate failure of the tool. In another example, the parameters of hydrocarbon production operations may be optimized. In yet another example, during exploration operations, the economics of a potential well may be evaluated where the presence of reactive components are taken into account, for example, by including the cost of corrosion-resistant tools and additional operations needed to properly treat or avoid reactive components. In another example, during sampling operations, the sensors described herein may be utilized to provide guidance as to how much sample to retrieve and from what depth along the wellbore to retrieve the sample.

Depending on where the sensors described herein are installed, the sensors may potentially be exposed to many different types of fluids over several wellbore operations. For example, sensors installed on casings or pipes may encounter oil-based muds, caustic cleaning fluids, acidic formation fluids, and hydrocarbon formation fluids. Since, as described herein, some sensors of the present disclosure are designed for specific environments (e.g., transmission techniques cannot be used with all fluids), more than one sensor may be installed. In some instances, each sensor may be associated with a flow path that opens and closes based on the fluid composition so as to mitigate wear of the sensor.

Figure 6:
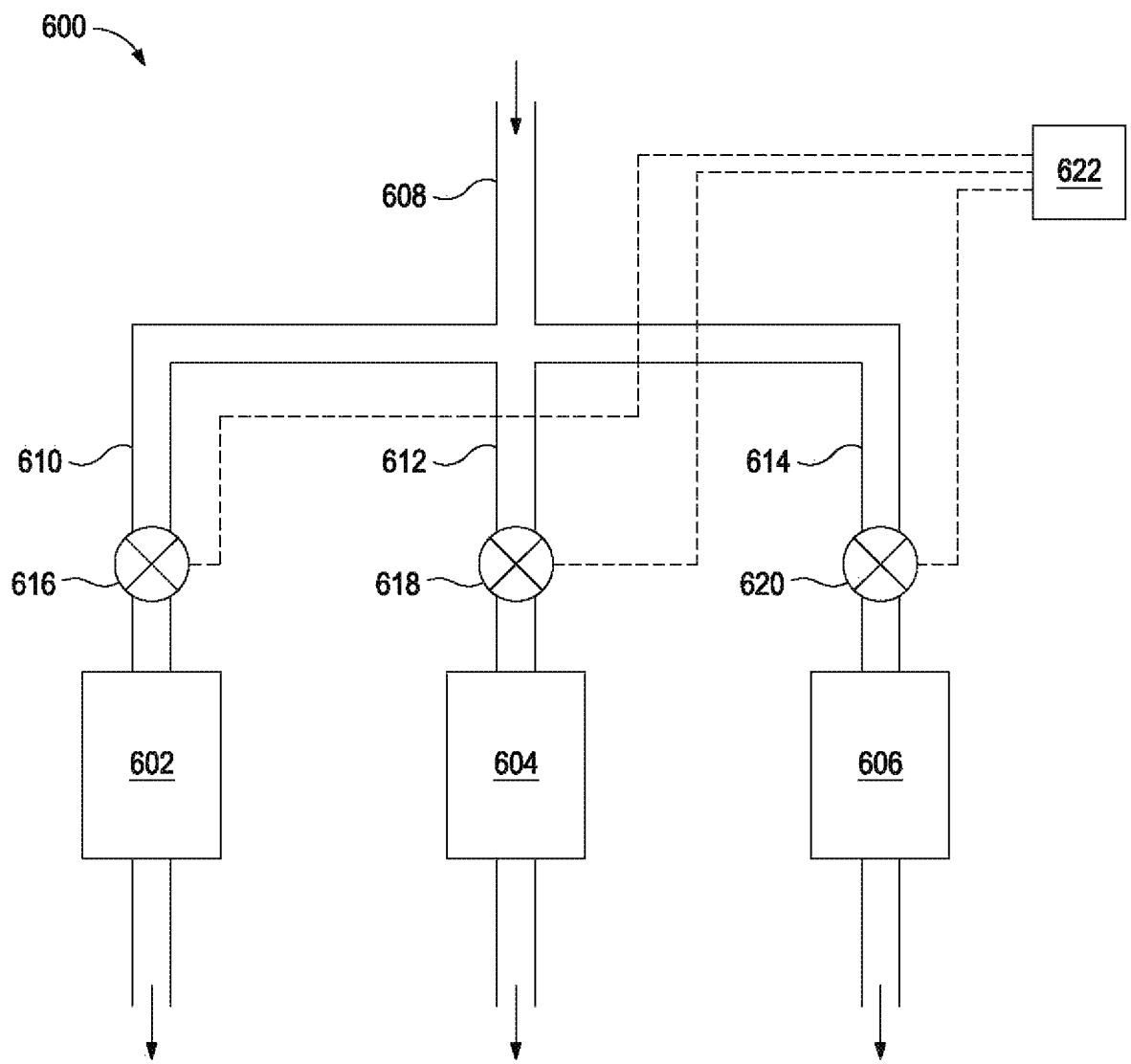
FIG. 6 illustrates a multi-sensor configuration according to at least some embodiments of the present disclosure.

FIG. 6 illustrates a multi-sensor configuration 600 according to at least some embodiments of the present disclosure. The illustrated multi-sensor configuration 600 includes three sensors 602,604,606 in parallel. The multi-sensor configuration 600 includes a series of flow paths with a primary flow path 608 that separates into three secondary flow paths 610,612,614 for each of the sensors 602,604,606, respectively. Each of the secondary flow paths 610,612,614 includes a valve 616,618,620 for allowing or stopping fluid flow to the respective sensors 602,604,606. The valves 616,618,620 are communicably coupled to a control system 622 that opens and closes each valve 616,618,620 to provide for fluid flow to the corresponding sensors 602,604,606. Control of which valves 616,618,620 are open and closed via the control system 622 may be done manually operated (i.e., via operator control), automatically operated (i.e., via computer control), or both. Decisions to open and close valves 602,604,606 may depend on the method of sensing the sensor is configured for, the reactive components the sensor is configured for, the composition of the fluid, the wellbore operation being undertaken, and the like.

In some embodiments, each of the sensors 602,604,606 may be configured for analyzing more than one reactive component (e.g., as described relative to FIGS. 1-4).

In some instances, the three sensors 602,604,606 may be operate by different sensing techniques. For example, a backside reflectance sensor 602, a transmission sensor 604, and an electrical sensor 606 may be used. Then, operation of the valves may be based on the composition of the fluid passing therethrough to appropriately match the sensing technique.

In some instances, the three sensors 602,604,606 may be a single type of sensor (e.g., backside reflectance, transmission, electrical, or combination). For example, if a specific reactive component is of interest, the first sensor 602 may be used until equilibrium is reached, then, the second sensor 604 may be used, and so on.

In some instances, each of the secondary flow paths 610,612,614 may lead to one or more sensors in series each for measuring one or more reactive components of interest. Further, while only three sensors are illustrated, in alternative embodiments, any number of sensors (e.g., two to fifty) may be included where the flow path configuration allows for any desired configuration of sensors to be in series, parallel, and combinations thereof.

In some instances, the multi-sensor configuration 600 may optionally further include flow paths and valves (not illustrated) for regenerating the sensors 602,604,606 (e.g., as described in FIG. 1).

In some instances, flow of the fluid to a sensor or sensor array may be facilitated by a pump fluidly coupled to the sensor. In some instances, fluid flow may rely on other mechanisms like pressure differentials resulting from temperature differences across the flow path through the sensor.

In some embodiments, the sensors described herein (e.g., those described relative to FIGS. 1-5 and variations thereof) may be coupled individual or as multi-sensor configurations to a variety of downhole tools and components. The sensors may be applicable to water monitoring for industrial use and disposal, for urban use and disposal, and for agricultural use and disposal. The sensors may also be applicable for pollution monitoring, industrial waste disposal, pipeline monitoring, monitoring of cargo undergoing shipping, refinery operations, petrochemical operations, and pharmaceutical operations.

Figure 7:
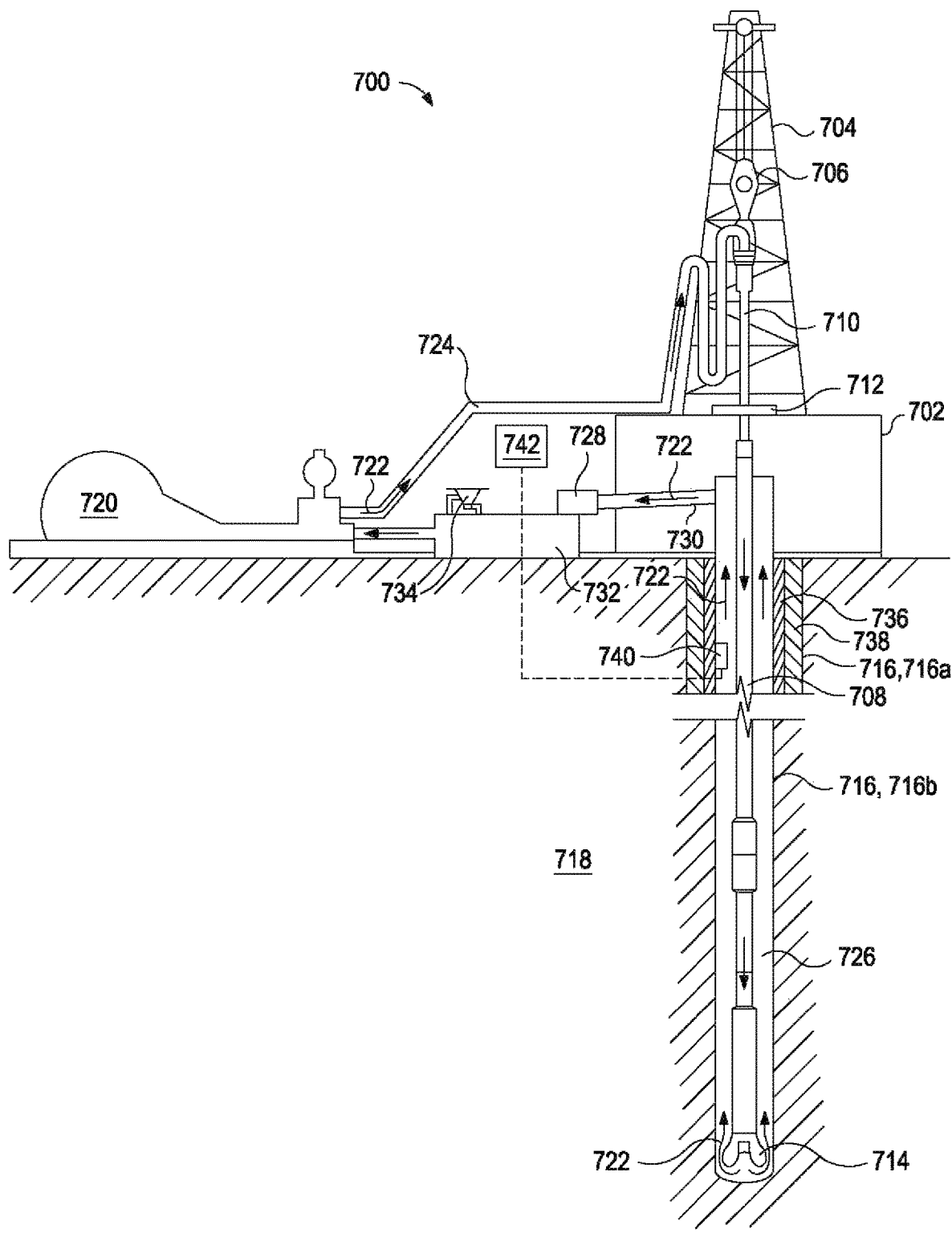
FIG. 7 is a wellbore drilling system in accordance with at least some of the embodiments of the present disclosure.

FIG. 7 is a wellbore drilling system 700 in accordance with at least some of the embodiments of the present disclosure. It should be noted that while FIG. 7 generally depicts a land-based drilling assembly, those skilled in the art will readily recognize that the principles described herein are equally applicable to subsea drilling operations that employ off-shore floating or sea-based platforms and rigs, without departing from the scope of the disclosure.

As illustrated, the drilling assembly 700 may include a drilling platform 702 that supports a derrick 704 having a traveling block 706 for raising and lowering a drill string 708. The drill string 708 may include, but is not limited to, drill pipe and coiled tubing, as generally known to those skilled in the art. A kelly 710 supports the drill string 708 as it is lowered through a rotary table 712. A drill bit 714 is attached to the distal end of the drill string 708 and is driven either by a downhole motor and/or via rotation of the drill string 708 from the well surface. As the bit 714 rotates, it creates a borehole 716 that penetrates various subterranean formations 718.

In the illustrated example, the borehole 716 includes two sections: a cased section 716*a* and an uncased section 716*b*.

The cased section 716*a* includes a casing 736 lining the wellbore 716 with a cement sheath 738 disposed therebetween.

A pump 720 (e.g., a mud pump) circulates drilling fluid 722 through a feed pipe 724 and to the kelly 710, which conveys the drilling fluid 722 downhole through the interior of the drill string 708 and through one or more orifices in the drill bit 714. The drilling fluid 722 is then circulated back to the surface via an annulus 726 defined between the drill string 708 and the walls of the borehole 716. At the surface, the recirculated or spent drilling fluid 722 exits the annulus 726 and may be conveyed to various surface treatment systems (e.g., fluid processing units, retention pits, mixers, and the like). As illustrated, the spent drilling fluid 722 is conveyed to a fluid processing unit 728 via an interconnecting flow line 730. Generally, the fluid processing unit 728 cleans the drilling fluid, for example, by removing drill cuttings the drilling fluid brought to the surface. The fluid processing unit 728 may include one or more of: a shaker (e.g., shale shaker), a centrifuge, a hydrocyclone, a separator (including magnetic and electrical separators), a desilter, a desander, a separator, a filter (e.g., diatomaceous earth filters), a heat exchanger, any fluid reclamation equipment, and the like, and any combination thereof. The fluid processing unit 728 may further include one or more sensors, gauges, pumps, compressors, and the like.

After passing through the fluid processing unit 728, a "cleaned" drilling fluid 722 is deposited into a nearby retention pit 732 (i.e., a mud pit). While illustrated as being arranged at the outlet of the wellbore 716 via the annulus 726, those skilled in the art will readily appreciate that the fluid processing unit 728 and retention pit 732 may be arranged at any other location in the drilling assembly 700 to facilitate its proper function, without departing from the scope of the disclosure.

Components of the drilling fluid 722 (e.g., weighting agents and fluid loss control additives) may be added to the drilling fluid 722 via a mixing hopper 734 communicably coupled to or otherwise in fluid communication with the retention pit 732. The mixing hopper 734 may include, but is not limited to, mixers and related mixing equipment known to those skilled in the art. In other embodiments, however, the drilling fluid components may be added to the drilling fluid 722 at any other location in the drilling assembly 700. In at least one embodiment, for example, there could be more than one retention pit 732, such as multiple retention pits 732 in series. Moreover, the retention pit 732 may be representative of one or more fluid storage facilities and/or units where the drilling fluid components may be stored, reconditioned, and/or regulated until added to the drilling fluid 722.

While not illustrated, the drilling assembly 700 may further include additional downhole equipment and tools that such as, but not limited to, floats, drill collars, mud motors, downhole motors and/or pumps associated with the drill string 708, and any measurement-while-drilling or logging-while-drilling (MWD/LWD) tools and related telemetry equipment, and sensors or distributed sensors associated with the drill string 708.

The drilling system 700 also includes a sensor or multi-sensor array 740 of the present disclosure coupled to the casing 736 in the cased section 716*a* of the wellbore 716. The sensor or multi-sensor array 740 is communicably coupled to a control system 742. Optionally, the sensor or multi-sensor array 740 may be fluidly coupled to a pump for facilitating fluid flow therethrough.

The control systems 742, control systems that may optionally be an integral portion of the sensor or multi-sensor array 740, and corresponding computer hardware used to implement the various illustrative blocks, modules, elements, components, methods, and algorithms described herein can include a processor configured to execute one or more sequences of instructions, programming stances, or code stored on a non-transitory, computer-readable medium. The processor can be, for example, a general purpose microprocessor, a microcontroller, a digital signal processor, an application specific integrated circuit, a field programmable gate array, a programmable logic device, a controller, a state machine, a gated logic, discrete hardware components, an artificial neural network, or any like suitable entity that can perform calculations or other manipulations of data. In some embodiments, computer hardware can further include elements such as, for example, a memory (e.g., random access memory (RAM), flash memory, read only memory (ROM), programmable read only memory (PROM), erasable programmable read only memory (EPROM)), registers, hard disks, removable disks, CD-ROMs, DVDs, or any other like suitable storage device or medium.

Executable sequences described herein can be implemented with one or more sequences of code contained in a memory. In some embodiments, such code can be read into the memory from another machine-readable medium. Execution of the sequences of instructions contained in the memory can cause a processor to perform the process steps described herein. One or more processors in a multi-processing arrangement can also be employed to execute instruction sequences in the memory. In addition, hard-wired circuitry can be used in place of or in combination with software instructions to implement various embodiments described herein. Thus, the present embodiments are not limited to any specific combination of hardware and/or software.

As used herein, a machine-readable medium will refer to any medium that directly or indirectly provides instructions to a processor for execution. A machine-readable medium can take on many forms including, for example, non-volatile media, volatile media, and transmission media. Non-volatile media can include, for example, optical and magnetic disks. Volatile media can include, for example, dynamic memory. Transmission media can include, for example, coaxial cables, wire, fiber optics, and wires that form a bus. Common forms of machine-readable media can include, for example, floppy disks, flexible disks, hard disks, magnetic tapes, other like magnetic media, CD-ROMs, DVDs, other like optical media, punch cards, paper tapes and like physical media with patterned holes, RAM, ROM, PROM, EPROM, and flash EPROM.

For example, the control system 742 described herein may be configured for receiving inputs from the sensor or multi-sensor array 740. The processor may also be configured to perform or reference mathematical calculations, lookup tables, and offset well data comparisons that are stored on the processor to derive the concentration of one or more reactive components in the fluid in contact with the sensor or multi-sensor array 740. In some instances, the processor may output a numerical value, graph, or the like indicative of the concentration, the concentration change over time, or the like. In some instances, the processor may change or suggest a change to the drilling fluid composition (e.g., adding additional scavengers to mitigate corrosion), the drilling operation parameters (e.g., using drill string 708 pipes that are more resistance to corrosion from the reactive components), or both based on the derived concentration of one or more reactive components in the fluid in contact with the sensor or multi-sensor array 740.

In some instances, the drilling assembly 700 may further comprise other sensors (not illustrated) that are communicably coupled to the control system 738. These sensors may provide real-time measurements of the temperature and flow rate of the fluid. These real-time measurements may optionally be used when deriving the concentration of one or more reactive components in the fluid in contact with the sensor or multi-sensor array 740 and/or when the processor makes a change or suggests a change to the drilling fluid composition, the drilling operation parameters, or both.

By having the sensor or multi-sensor array 740 coupled to the casing 736, the sensor or multi-sensor array 740 may optionally be used to analyze the concentration of reactive components in the fluids associated with subsequent wellbore operations. Exemplary operations may include, but are not limited to wireline logging operations, MWD/LWD operations, hydraulic fracturing operations, acidizing operations, production operations, and the like.

Additionally, one or more sensors and/or multi-sensor arrays may be coupled to other components of drilling systems or systems used for other operations, for example, MWD/LWD tools, wireline tools, the drill string, other tubulars like production tubing or coiled tubing, sliding sleeves, perforation guns, screens, frac plugs, packers, and the like. For example, one or more sensors and/or multi-sensor arrays may be located in a side pocket mandrel of a tubular.

Figure 8:
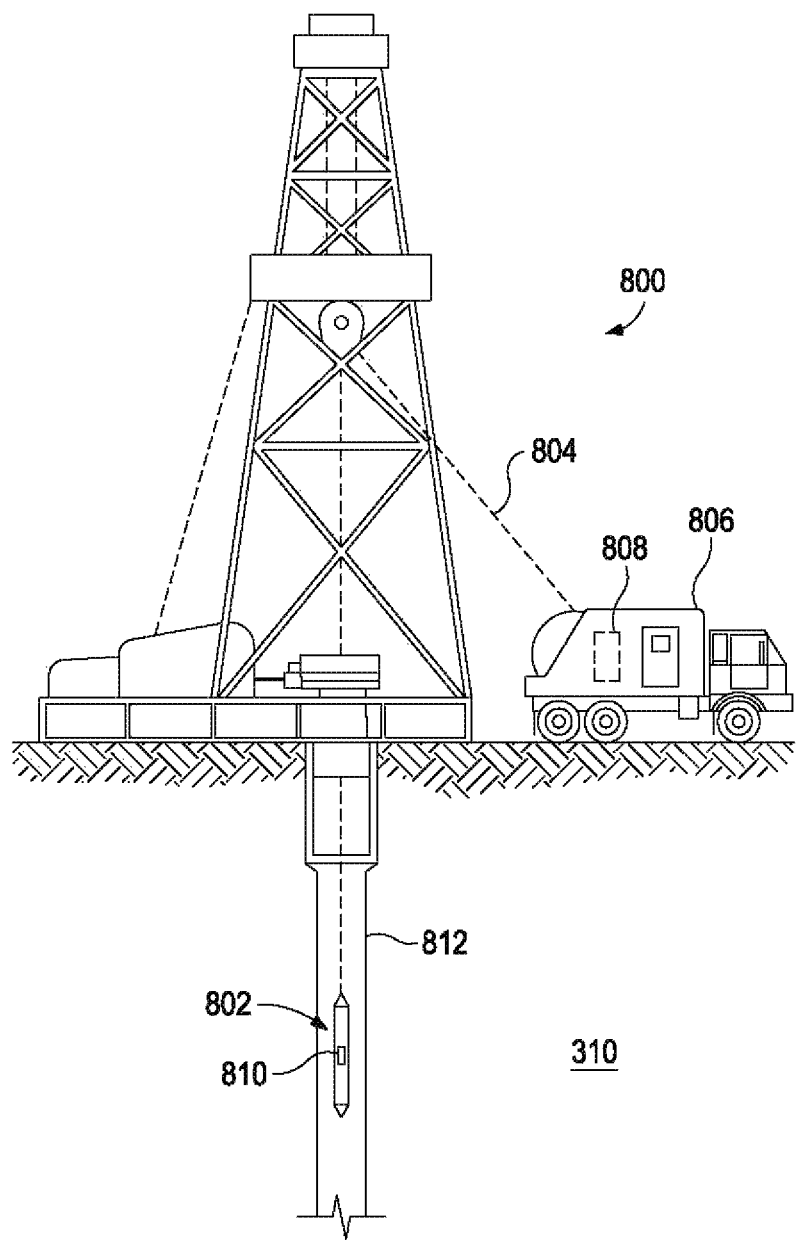
FIG. 8 depicts a schematic diagram of an exemplary wireline system.

For example, at various times during or after the drilling process, including after stimulation operations, the drill string 708 or other apparatus extending into the wellbore (e.g., a work string for perforating the formation) may be removed from the wellbore 812, as shown in FIG. 8, to conduct measurement/logging operations. More particularly, FIG. 8 depicts a schematic diagram of an exemplary wireline system 800 that may employ the principles of the present disclosure, according to one or more embodiments. Like numerals used in FIGS. 7 and 8 refer to the same components or elements and, therefore, may not be described again in detail. As illustrated, the wireline system 800 may include one or more wireline tools 802 that may be suspended in the wellbore 812 (illustrated as an open hole wellbore without a casing) by a cable 804. The wireline tools 802 may include one or more sensors and/or multi-sensor arrays 810 where the wireline tools 802 and the sensors/arrays 810 are communicably coupled to the cable 804. The cable 804 may include conductors for transporting power to the wireline tools 802 and the sensors/arrays 810 and also facilitate communication between the surface and the wireline tools 802 and the sensors/arrays 810. A logging facility 806, shown in FIG. 8 as a truck, may collect measurements from the wireline tools 802, and may include computing facilities 808 for controlling, processing, storing, and/or visualizing the measurements gathered by the wireline tools 802. The computing facilities 808 may be communicably coupled to the wireline tools 802 by way of the cable 804. In some instances, the computing facilities 808 may include a control system similar to the control system 742 described above.

Optionally, the sensors/arrays 810 may be fluidly coupled to a pump for facilitating fluid flow therethrough. For example, the wireline tools 802 may include the pump, and the computing facilities 808 may transmit instructions to the pump when to flow fluid and to the sensor when to collect data.

In each of the foregoing drilling and wireline systems, the methods and processes described herein (or portions thereof) that utilize the sensors and sensor arrays of the present disclosure to measure a concentration of the reactive component may be implemented on-site (e.g., at a computer or processor on-site like the computing facilities 808 illustrated in the wireline system of FIG. 8 or a similar computing facility at the drilling system of FIG. 7). Alternatively or in conjunction therewith, the methods and processes described herein (or portions thereof) that utilize the sensors and sensor arrays of the present disclosure to measure a concentration of the reactive component may be performed off-site where the data from the sensors or sensor arrays are transmitted (wired or wirelessly) or physically delivered to the off-site location.

While the sensors and/or multi-sensor arrays may be useful in sensing reactive components in fluids downhole, the sensors and/or multi-sensor arrays may also be implemented in surface locations like at the pump, the retention pit, the fluid processing unit, and the like.

In some instances, the sensors or sensor arrays of the present disclosure may be implemented.

Embodiments of the present disclosure include, but are not limited to, Embodiment A, Embodiment B, Embodiment C, and Embodiment D.

Embodiment A is a method that comprises contacting a sensing component of a sensor with a fluid comprising a reactive component, the sensing component comprising a reactive surface on a substrate; physisorbing, chemisorbing, or both the reactive component to the reactive surface thereby causing a change to a band gap of the reactive surface; measuring one selected form the group consisting of the change to the band gap of the reactive surface, a rate of the change to the band gap of the reactive surface, and a combination thereof; and deriving a concentration of the reactive component in the based on the one selected form the group consisting of the change to the band gap of the reactive surface, the rate of the change to the band gap of the reactive surface, and the combination thereof. Optionally, Embodiment A may further include one or more of the following: Element 1: wherein the sensor further comprises a light source and a detector, and wherein the method further comprises: transmitting light from the light source through the substrate to the reactive surface to produce reflected interacted light that is indicative of the band gap of the reactive surface; and measuring the reflected interacted light with the detector; Element 2: wherein the sensor further comprises a light source and a detector, and wherein the method further comprises: transmitting light from the light source through the substrate and reactive surface to produce transmitted interacted light that is indicative of the band gap of the reactive surface; and measuring the transmitted interacted light with the detector; Element 3: wherein the sensor further comprises a electrical leads contacting the reactive surface and a detector communicably coupled to the electrical leads, and wherein the method further comprises: measuring a conductance of the reactive surface that is indicative of the band gap of the reactive surface; Element 4: wherein the sensor is one of a plurality of sensors (e.g., a portion of a sensor array) where the plurality of sensors include at least one selected from the group consisting of Element 1, Element 2, Element 3, two or more of Elements 1-3 in combination to form a combination sensor, and any combination thereof; Element 5: the method further comprising regenerating the reactive surface; and repeating the method to derive a second concentration of the reactive component; Element 6: wherein the sensor is coupled to a wellbore tool within a wellbore penetrating a subterranean formation, and wherein the method further comprises: performing a wellbore operation; and changing a parameter of the wellbore operation based on the concentration of the reactive component; Element 7: wherein the sensor is coupled to a wellbore tool within a wellbore penetrating a subterranean formation, and wherein the method further comprises: calculating a cumulative amount of the reactive species based on the concentration of the reactive component over time; and replacing the wellbore tool when the cumulative amount reaches a threshold; Element 8: wherein the sensor is fluidly coupled to a pump configured to flow a fluid through the sensor for analysis; Element 9: wherein the reactive surface comprises one selected from the group consisting of gold, nickel, copper, molybdenum, aluminum, tungsten, titanium, and any combination thereof; Element 10: wherein a thickness of the reactive surface varies across the substrate; Element 11: wherein the reactive surface comprises a matrix that is nonreactive to the reactive component and is doped with particles that are reactive to the reactive component; and Element 12: wherein the reactive surface comprises particles substantially in a monolayer on the substrate. Exemplary combinations of elements may include, but are not limited to, one of Elements 1-4 in combination with one or more of Elements 5-8; one of Elements 1-4 in combination with one or more of Elements 9-12; one or more of Elements 5-8 in combination with one or more of Elements 9-12; two or more of Elements 5-8 in combination; and two or more of Elements 9-12 in combination.

Embodiment B is a system that comprises a wellbore tool suspended in a wellbore penetrating a subterranean formation by a cable; a sensor coupled to the wireline tool; and wherein the sensor is one selected from the group consisting of: (A) a backside reflectance sensor comprising a first light source, a first detector, and a first sensing component that itself comprises a first reactive surface on a first substrate, wherein the backside reflectance sensor is configured such that first light from the first light source passes through the first substrate to the first reactive surface to produce reflected interacted light that is indicative of a band gap of the first reactive surface and is detected by the first detector; (B) a transmission sensor comprising a second light source, a second detector, and a second sensing component that itself comprises a second reactive surface on a second substrate, wherein the transmission sensor is configured such that second light from the second light source passes through the second substrate and the second reactive surface to produce transmitted interacted light that is indicative of a band gap of the second reactive surface and is detected by the second detector; (C) an electrical sensor comprising a third detector, electrical leads, and a third sensing component that itself comprises a third reactive surface on a third substrate, wherein the electrical leads are in contact with the reactive surface and are communicably coupled to the third detector, and wherein the electrical sensor is configured such that the third detector measures a conductance of the reactive surface that is indicative of a band gap of the third reactive surface; and (D) any combination of (A), (B), and (C) as a combination sensor. Optionally, Embodiment B may further include one or more of the following: Element 8; Element 9; Element 10; Element 11; Element 12; Element 13: wherein the sensor is a component of a sensor array; and Element 14: wherein the sensor is a component of a sensor array, the sensor is a first sensor and the sensor array comprises a second sensor selected from the group consisting of (A), (B), (C), and (D). Exemplary combinations of elements may include, but are not limited to, Elements 8, 13, and 14 (alone or in any combination) in combination with one or more of Elements 9-12; two or more of Elements 9-12 in combination; and two or more of Elements 8, 13, and 14 in combination.

Embodiment C is a system that comprises a tubular extending into a wellbore penetrating a subterranean formation; a sensor coupled to one selected from the group consisting of: the tubular, a wellbore tool disposed in the wellbore, and a combination thereof; and wherein the sensor is one selected from the group consisting of: (A) a backside reflectance sensor comprising a first light source, a first detector, and a first sensing component that itself comprises a first reactive surface on a first substrate, wherein the backside reflectance sensor is configured such that first light from the first light source passes through the first substrate to the first reactive surface to produce reflected interacted light that is indicative of a band gap of the first reactive surface and is detected by the first detector; (B) a transmission sensor comprising a second light source, a second detector, and a second sensing component that itself comprises a second reactive surface on a second substrate, wherein the transmission sensor is configured such that second light from the second light source passes through the second substrate and the second reactive surface to produce transmitted interacted light that is indicative of a band gap of the second reactive surface and is detected by the second detector; (C) an electrical sensor comprising a third detector, electrical leads, and a third sensing component that itself comprises a third reactive surface on a third substrate, wherein the electrical leads are in contact with the reactive surface and are communicably coupled to the third detector, and wherein the electrical sensor is configured such that the third detector measures a conductance of the reactive surface that is indicative of a band gap of the third reactive surface; and (D) any combination of (A), (B), and (C) as a combination sensor. Optionally, Embodiment B may further include one or more of the following: Element 8; Element 9; Element 10; Element 11; Element 12; Element 13; Element 14; Element 15: wherein the wellbore tool is a casing lining the wellbore and the sensor is coupled to the casing; and Element 16: wherein the tubular includes a fluid entrance and the sensor is located at the fluid entrance. Exemplary combinations of elements may include, but are not limited to, Elements 8, 13, 14, 15, and 16 (alone or in any combination) in combination with one or more of Elements 9-12; two or more of Elements 9-12 in combination; and two or more of Elements 8, 13, 14, 15, and 16 in combination.

Unless otherwise indicated, all numbers expressing quantities of ingredients, properties such as molecular weight, reaction conditions, and so forth used in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present invention. At the very least, and not as an attempt to limit the application of the doctrine of equivalents to the scope of the claim, each numerical parameter should at least be construed in light of the number of reported significant digits and by applying ordinary rounding techniques.

One or more illustrative embodiments incorporating the invention embodiments disclosed herein are presented herein. Not all features of a physical implementation are described or shown in this application for the sake of clarity. It is understood that in the development of a physical embodiment incorporating the embodiments of the present invention, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for those of ordinary skill in the art and having benefit of this disclosure.

While compositions and methods are described herein in terms of "comprising" various components or steps, the compositions and methods can also "consist essentially of" or "consist of" the various components and steps.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces.

The invention claimed is:

1. A method for performing downhole measurements using a wellbore system, comprising:
measuring, in a downhole environment of a wellbore, at least one of a change of a bandgap and a rate of change of the bandgap of a reactive surface of a sensor of a wellbore system after the reactive surface of the sensor is contacted by a fluid having a reactive component, wherein the band structure of the reactive surface of the sensor is changed by the reactive component in the fluid; and
determining a concentration of the reactive component in the fluid based, at least in part, on the at least one of the change in the bandgap and the rate of change of the bandgap of the reactive surface.

2. The method of claim 1, wherein the measuring comprises:
illuminating the reactive surface via light emitted by a light source;

detecting interacted light, wherein the interacted light is a product of reflection or transmission of the illuminating light and the reactive surface; and determining the at least one of the change of the bandgap and the rate of change of the bandgap based, at least in part, on the interacted light.

3. The method of claim 2, wherein the measuring further comprises:

determining at least one of intensity, wavelength, and frequency of the interacted light.

4. The method of claim 1, further comprising:

measuring an electrical property of the reactive surface, wherein determining the concentration of the reactive component comprises determining the concentration of the reactive component based, at least in part, on the electrical property of the reactive surface.

5. The method of claim 4, wherein measuring an electrical property of the reactive surface comprises measuring a conductance or a resistance of the reactive surface, and wherein determining the concentration of the reactive component based, at least in part, on the electrical property comprises determining the concentration of the reactive component based, at least in part, on the measured conductance or the measured resistance of the reactive surface.

6. The method of claim 1, further comprising:

measuring at least one of a second change of a bandgap and a second rate of change of the bandgap of the reactive surface; and determining a second concentration of the reactive component in the fluid based, at least in part, on the at least one of the second change in the bandgap and the second rate of change of the bandgap of the reactive surface.

7. The method of claim 6, further comprising:

calculating, based on the determined concentration and the determined second concentration, at least one of a concentration of the reactive component over time and a cumulative amount of the reactive component; and determining a parameter of wellbore operation based on the at least one of the concentration of the reactive component over time and a cumulative amount of the reactive component, wherein the parameter of wellbore operation comprises at least one of a wellbore tool lifetime, a wellbore tool replacement threshold, and a reactive component threshold.

8. The method of claim 1, further comprising:

regenerating the reactive surface, wherein the regeneration comprises desorbing the reactive component from the reactive surface;

measuring at least one of a third change of a bandgap and a third rate of change of the bandgap of the reactive surface; and determining a concentration of the reactive component in the fluid based, at least in part, on the at least one of the third change in the bandgap and the third rate of change of the bandgap.

9. The method of claim 8, wherein desorbing the reactive component from the reactive surface comprises:

at least one of heating the reactive surface and supplying a purge fluid to the reactive surface.

10. The method of claim 1, wherein determining a concentration of the reactive component in the fluid comprises determining a concentration of at least one of hydrogen sulfide, mercury, carbon dioxide, an acid, and a base.

11. The method of claim 1, further comprising:

adjusting at least one parameter of a wellbore operation based on the determined concentration of the reactive component in the fluid.

12. The method of claim 1, wherein the reactive surface comprises at least one of gold, nickel, copper, molybdenum, aluminum, tungsten, titanium, and a nonreactive matrix doped with particles reactive to the reactive component.

13. An apparatus of a wellbore system deployed in a wellbore, comprising:

at least one detector;
at least one light source;
a substrate;
a reactive surface on the substrate;
a sensor;
a processor; and
a computer-readable medium having instructions stored thereon that are executable by the processor to cause the apparatus to,
determine at least one of a change of a bandgap and a rate of change of the bandgap of the reactive surface of the substrate of the apparatus of the wellbore system after the reactive surface is contacted by a fluid having a reactive component, wherein the band structure of the reactive surface is changed by the reactive component in the fluid, and
determine a concentration of the reactive component in the fluid based, at least in part, on the at least one of the change in the bandgap and the rate of change of the bandgap of the reactive surface.

14. The apparatus of claim 13, wherein the sensor is fluidically coupled to a pump, and wherein the pump provides the fluid contacting the reactive surface.

15. The apparatus of claim 13, wherein the reactive surface comprises at least one of gold, nickel, copper, molybdenum, aluminum, tungsten, titanium, and a nonreactive matrix doped with particles reactive to the reactive component of the fluid.

16. The apparatus of claim 13, wherein the reactive surface varies in thickness.

17. The apparatus of claim 13, wherein the reactive surface comprises particles arranged substantially in a monolayer on a substrate.

18. The apparatus of claim 13, wherein the reactive surface comprises two or more types of particles and wherein each particle type is reactive to at least one reactive component of the fluid.

19. An apparatus of a wellbore system, comprising:

a processor; and
a computer-readable medium having instructions stored thereon that are executable by the processor to cause the apparatus to,
measure, in a downhole environment of a wellbore, at least one of a change of a bandgap and a rate of change of the bandgap of a reactive surface of a sensor of the wellbore system after the reactive surface of the sensor is contacted by a fluid having a reactive component, wherein the band structure of the reactive surface of the sensor is changed by the reactive component in the fluid, and
determine a concentration of the reactive component in the fluid based, at least in part, on the at least one of the change in the bandgap and the rate of change of the bandgap of the reactive surface.

20. The apparatus of claim 19, wherein the instructions further compromise instructions to measure at an electrical property of the reactive surface based, at least in part, on electrical signals received from the reactive surface, and
wherein the instructions to determine the concentration of the reactive component further compromise instructions to determine the concentration of the reactive component based, at least in part, to measure the electrical property of the reactive surface.

* * * * *